United States Patent
Roue

(10) Patent No.: US 6,350,270 B1
(45) Date of Patent: Feb. 26, 2002

(54) ANEURYSM LINER

(75) Inventor: Chad C. Roue, Fremont, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/490,788

(22) Filed: Jan. 24, 2000

(51) Int. Cl.$^7$ ............................................... A61B 17/12
(52) U.S. Cl. ....................................... 606/151; 606/195
(58) Field of Search ............................... 606/191, 158, 606/151, 200, 198; 623/1.13, 1.23

(56) References Cited

U.S. PATENT DOCUMENTS

| 5,334,210 A | * | 8/1994 | Gianturco | 606/151 |
| 5,522,822 A | * | 6/1996 | Phelps et al. | 606/151 |
| 5,861,003 A | * | 1/1999 | Latson et al. | 606/213 |
| 5,916,235 A | * | 6/1999 | Guglielmi | 606/200 |

FOREIGN PATENT DOCUMENTS

| WO | WO 96/01591 | | 1/1996 |
| WO | WO 99/03404 | | 1/1999 |
| WO | WO-99/034304 | * | 1/1999 |
| WO | WO 99/05977 | | 2/1999 |
| WO | WO 99/42059 | | 8/1999 |

* cited by examiner

Primary Examiner—Kennedy Schaetzle
Assistant Examiner—Kristen Droesch
(74) Attorney, Agent, or Firm—Joseph R. Kelly; Westman, Champlin & Kelly, P.C.

(57) ABSTRACT

An improved aneurysm liner is used for treating an aneurysm in a parent vessel. The parent vessel defines a lumen. The aneurysm includes a neck and an inner wall defining a cavity in fluid communication with the lumen. The liner device is configured for deployment within the cavity. The device includes an extender inside an expandable aneurysm liner. The proximal pusher end of the extender receives force from a distal end of a delivery catheter for maneuvering the device into a deployment position. The device is arranged such that, when deployed within the cavity, the liner is expanded to fill the cavity. In treating an aneurysm, the liner device is directed to the aneurysm site by a guidewire that extends through the extender. Upon removal of the guidewire, the extender is released within the liner and the liner is expanded to fill the cavity.

28 Claims, 6 Drawing Sheets

ANEURYSM LINER

BACKGROUND OF THE INVENTION

The present invention deals with a system for treating an aneurysm. More specifically, the present invention is directed to a system for deployment of an aneurysm liner within the aneurysm.

An aneurysm is a localized stretching or distension of an artery due to a weakening of the vessel wall. For example, "berry" aneurysms, i.e., small spherical distensions, occur in the vessels of the brain. The distensions—often referred to as the aneurysm sac—are related to defects in the muscular coating of the artery and are probably degenerative in origin. Rupture of aneurysms account for the majority of spontaneous hemorrhages. Approximately 25,000 intracranial aneurysms rupture every year in North America.

Several methods of treating aneurysms have been attempted, with varying degrees of success. At present, the treatment of aneurysms with drugs is substantially ineffective. Also, extra-vascular surgery, referred to as open craniotomy, for the purpose of preserving the parent artery is replete with disadvantages. A patient subject to open craniotomy for intercranial aneurysms typically must undergo general anesthesia, surgical removal of part of the skull, brain retraction, dissection around the neck of the sac, and placement of a clip on the parent artery to prevent bleeding or rebleeding.

Alternative treatments include endovascular occlusion where the interior of the aneurysm is entered with a guidewire or a microcatheter. An occlusion is formed within the sac with an intention to preserve the parent artery. A preferred means for forming a mass is through the introduction of an embolic agent within the sac. Examples of embolic agents include a detachable coil, which is detached from the end of a guidewire, and a liquid polymer which polymerizes rapidly on contact with blood to form a firm mass.

Endovascular occlusion is not without drawbacks. For example, there is a risk of overfilling the sac and consequent embolic agent migration into the parent vessel. overfilling of the sac also generates additional pressure in the aneurysm.

Another means for forming a mass in the aneurysm sac involves the placement of an expandable balloon or liner in the aneurysm. Detachable occlusion balloons have been used for a number of medical procedures. These balloons are carried at the end of a catheter and, once inflated can be detached from the catheter. Such a balloon may be positioned within an aneurysm, filled and then detached from the catheter. Deploying the balloon within the aneurysm can be rather difficult due to the high rates of blood flow through the aneurysm. Elastic balloons have exhibited problems with respect to performance and have not been used endovascularly in some time.

This aneurysm filling technique also has its problems. As the balloon is filled, the operator must be very careful not to overfill the balloon due to possible risk of rupturing the aneurysm. Accordingly, the balloon may be too small, potentially resulting in the release of the balloon from the aneurysm into the blood stream. Furthermore, the balloon often does not mold or shape to the odd-shaped contours of the aneurysm leaving room for blood to continue flowing through the aneurysm, or generating undesired pressure on the aneurysm wall.

Aneurysm liners are composed of a liner sac which is placed in the aneurysm and filled to occlude the aneurysm. A guidewire is inserted in the liner. The guidewire carries the liner through the vasculature to deploy the liner in the aneurysm.

The delivery and deployment of aneurysm liners pose similar problems to the occlusion balloons. In addition, current aneurysm liners require the use of specific guidewires in order to hold the liner in a low profile position so it can be advanced through the vasculature. The guidewire is required to be extended distally of the liner by a fixed amount when the liner is introduced into the aneurysm. This makes it difficult to place the liner in the aneurysm and requires a "bumper" on the wire to contact a marker band and extend the sac or liner. Further, the extension of the guidewire past the distal end of the sac can be problematic when placing the sac into an aneurysm as the extended tip can increase the risk of rupturing the aneurysm.

SUMMARY OF THE INVENTION

An improved aneurysm liner is used for treating an aneurysm in a parent vessel. The parent vessel defines a lumen. The aneurysm includes a neck and an inner wall defining a cavity in fluid communication with the lumen. The liner device is configured for deployment within the cavity. The device includes an extender inside an expandable aneurysm liner. The proximal extender end receives force from a distal end of a delivery catheter for maneuvering the device into a deployment position. The device is arranged such that, when deployed within the cavity, the liner expands to fill the cavity.

In treating an aneurysm, the liner device is directed to the aneurysm site by a guidewire that extends through the extender. Upon removal of the guidewire, the extender is released within the liner and the liner is allowed to relax. The liner is then expanded, by introducing embolic material therein, to fill the cavity.

DETAILED DESCRIPTION OF THE ILLUSTRATIVE EMBODIMENTS

Figure 1:
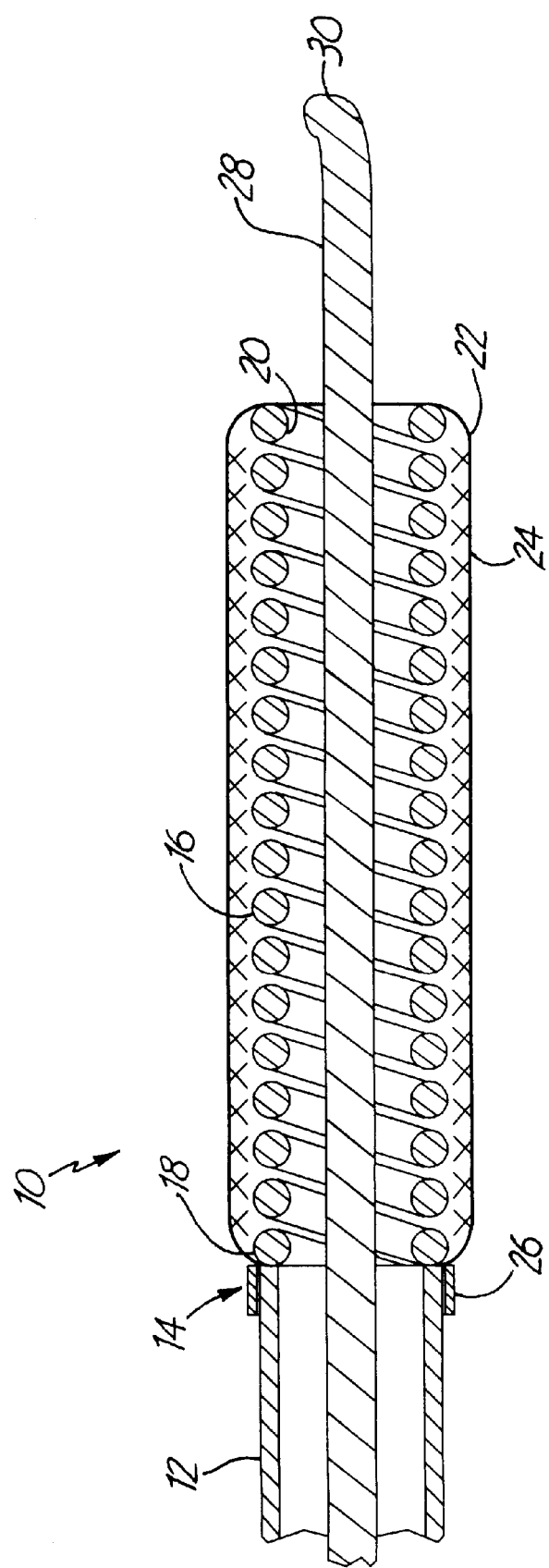
FIG. 1 is a side view of a portion of an aneurysm treatment device in accordance with one embodiment of the present invention.

FIG. 1 is a side view of a portion of an aneurysm treatment device 10 in accordance with the present invention. Device 10 includes delivery catheter 12, extender coil 16 and expandable liner 24. Delivery catheter 12 has a proximal end which extends proximally to a position where it is manipulable by an operator. Delivery catheter 12 also has a distal end 14. Extender coil 16 has a proximal end 18 and a distal end 20.

Wherein the insertion position shown in FIG. 1, extender coil 16 is aligned at its proximal end 18 with the distal end 14 of delivery catheter 12. In one embodiment, coil 16 is not physically connected to liner 24, but floats therein when not disposed over a guidewire. In another embodiment, the distal end 20 of extender coil 16 is attached to the distal end 22 of expandable liner 24, or the proximal end 18 of coil 16 is attached to the proximal end 32 of liner 24. Various methods of permanently attaching coil 16 to liner 24 can be used such as sewing, threading coil 16 into a weave of liner 24, ultrasonic bonding, crimping marker bands, welding or adhesives.

In the embodiment described first, the distal end of coil 16 is attached to the distal end of liner 24. In that embodiment, the expandable liner 24 extends proximally from its connection to the distal end of the extender coil 16 towards the catheter 12. Liner 24 has a proximal opening or mouth which, in one embodiment, is removably attached to the distal end 14 of catheter 12 with a suitable technique such as proximal marker bands 26, the well known Guglielmi detachment mechanism, or another temporary connection mechanism.

FIG. 1 shows extender coil 16 coaxially aligned with catheter 12, and guidewire 28 disposed through the lumen defined by the interior of catheter 12 and extender coil 16. In this position, since the distal end of liner 24 is connected to the distal end of coil 16, liner 24 is lengthened axially and is thus held in a radially collapsed position.

Guidewire 28 extends distally through catheter 12 and extender coil 16. The distal end 30 of guidewire 28 is directed transluminally to a treatment sight and is used to guide the aneurysm treatment device 10 into position for deployment. The extender coil 16 is held in an axially aligned conformation by guidewire 28 such that the coil 16 conforms to the curvature of the guidewire 28. The extender coil 16, rather than the guidewire 28, acts to extend and even tension the liner 24. Thus, the guidewire 28 is then free to move axially through the extender coil while positioning and deploying the liner 24 in the aneurysm without the risk of rupture.

Figure 2:
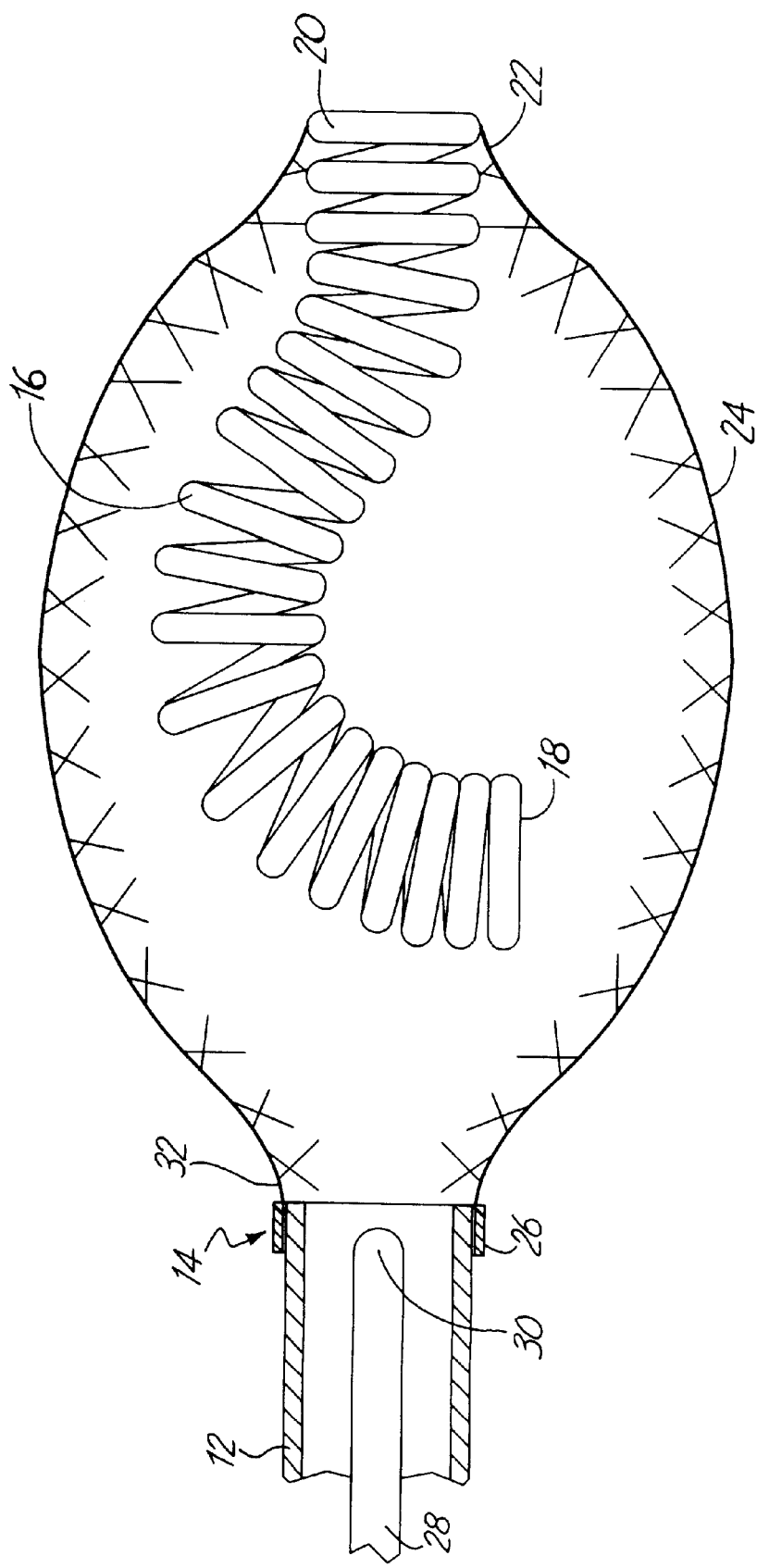
FIG. 2 is a side view of the aneurysm treatment device shown in FIG. 1 in an expanded position.

FIG. 2 shows similar items as those shown in FIG. 1, and they are similarly numbered. However, in FIG. 2, guidewire 28 has been retracted proximally such that its distal end 30 is in a position proximal of the distal end 14 of catheter 12. Retraction of the guidewire 28 from the extender coil 16 allows the proximal end 18 of coil 16 unrestricted motion inside the aneurysm liner 24. In one illustrative embodiment, extender coil 16 is made of stainless steel or a radiopaque material (such as platinum), for purposes of visualization, but can be made of a polymer or some other material as well. Coil 16 can also be biased in a helical shape or another shape which causes its proximal end 18 to move away from the proximal end 32 of liner 24. Of course, coil 16 can simply be highly flexible such that it falls away from the proximal end 32 of liner 24 when guidewire 28 is removed to release the proximal end 18 of coil 16. With the proximal end 18 of extender coil 16 in the position shown in FIG. 2, a method for expanding the liner 24, such as filling the liner with an embolic agent, can be performed.

The releasable connection between the proximal end 32 of liner 24 and the distal end 14 of catheter 12 provides communication between the interior of liner 24 and the lumen in catheter 12. This allows the expandable liner 24 to be held in place at the treatment site and filled to a desired capacity before the liner 24 is released from catheter 12, as is discussed in greater detail below.

Figure 3:
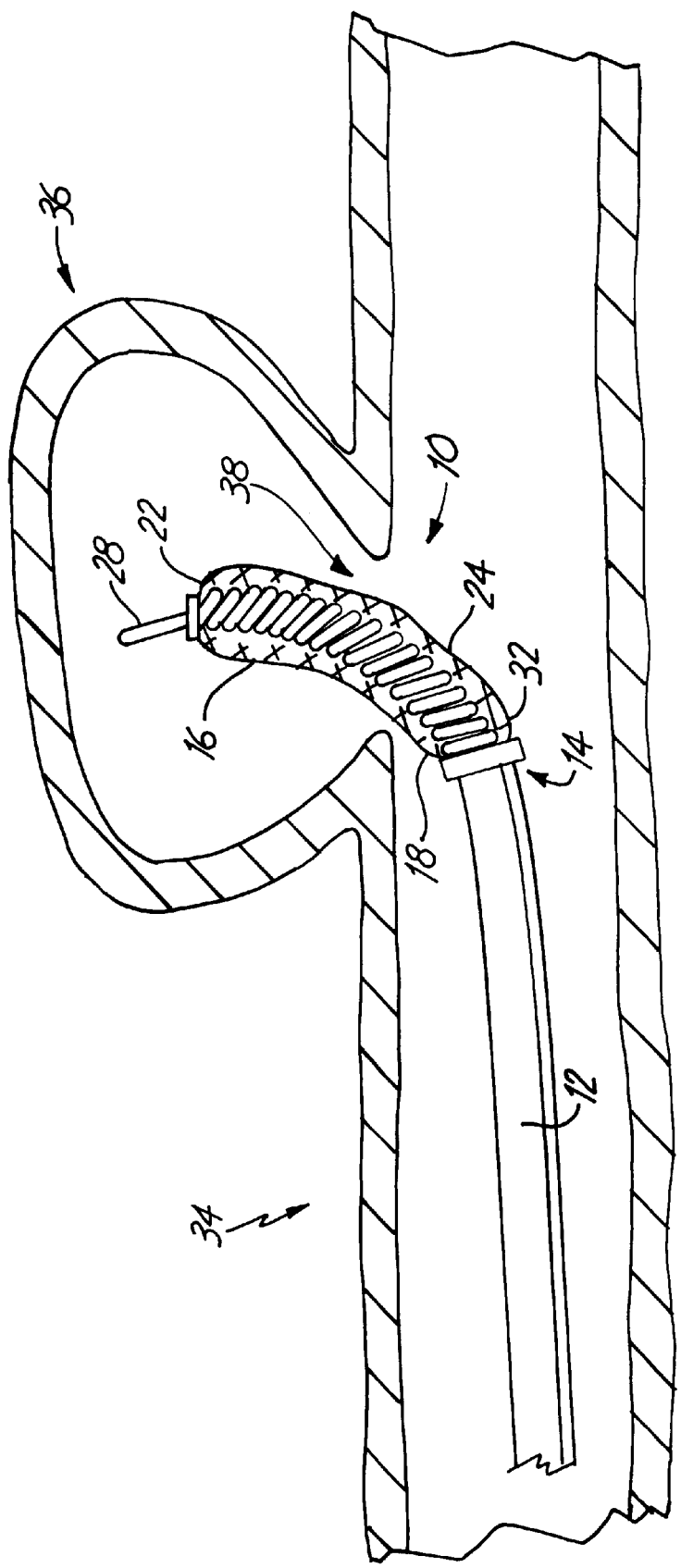
FIG. 3 illustrates the positioning of the aneurysm treatment device shown in FIG. 1 prior to deployment during the treatment of an aneurysm.
Figure 4:
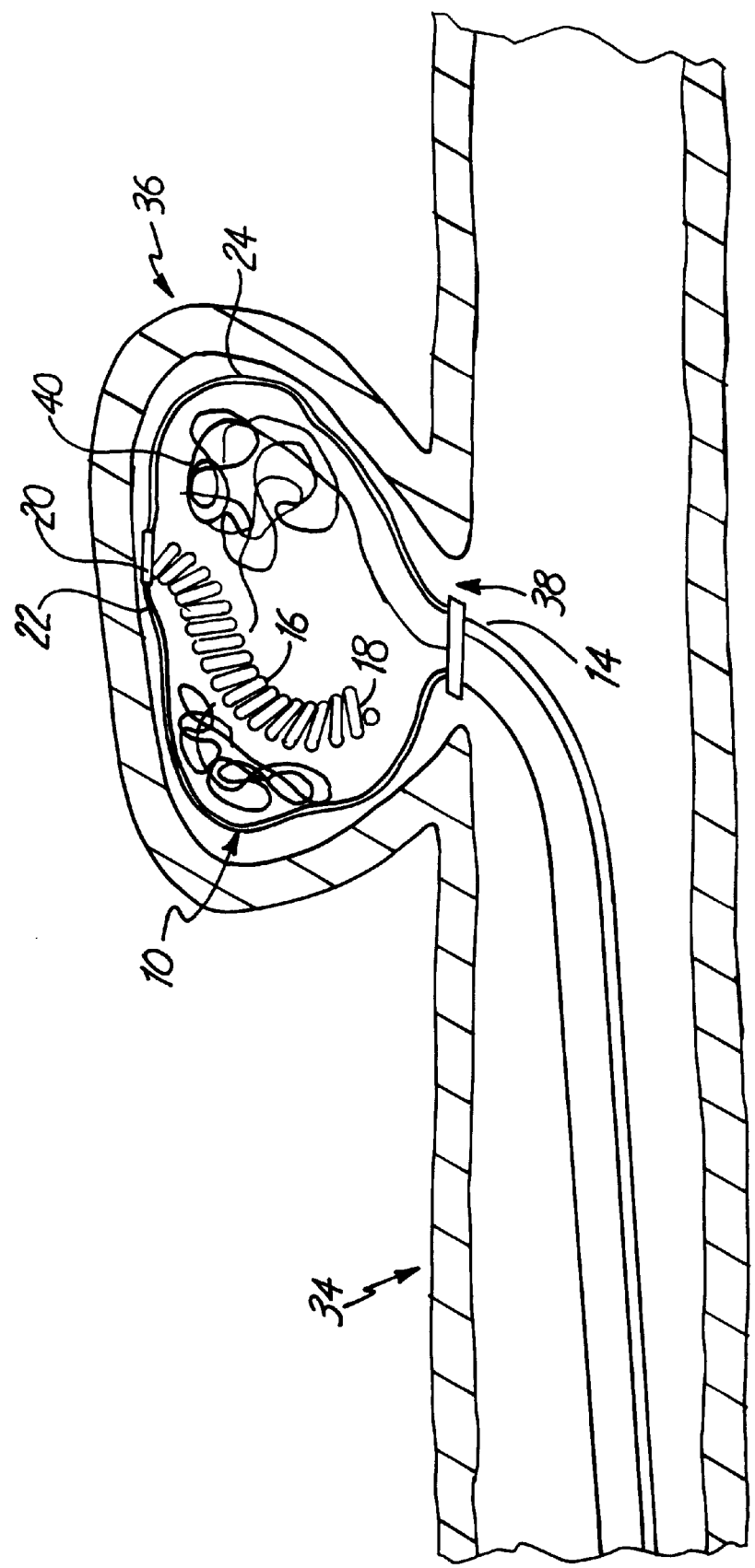
FIG. 4 illustrates the deployment and expansion of the aneurysm treatment device shown in FIG. 1 during the treatment of an aneurysm.

FIGS. 3 and 4 better illustrate the operation of aneurysm treatment device 10. FIG. 3 illustrates positioning of the aneurysm treatment device through a vessel 34 into an aneurysm 36 prior to deployment of the device. Aneurysm treatment device 10 can be pre-loaded or back-loaded onto guidewire 28. Guidewire 28 is manipulated through the vasculature from the entry site (such as the femoral artery) to the region of vessel 34 containing the aneurysm. The distal tip of guidewire 28 is advanced across the neck of the aneurysm and into the aneurysm sac. This can be done using any desirable visualization technique.

In one embodiment, catheter 12 is placed over guidewire 28 prior to positioning guidewire 28 in the vasculature, with several centimeters of guidewire 28 extending distal of the distal tip of catheter 12. Therefore, when the distal end of guidewire 28 has passed the aneurysm neck 38, catheter 12 is positioned just proximal of neck 38. Treatment device 10 is then advanced into the aneurysm sac.

In another embodiment, guidewire 28 is placed in the vasculature first. Once the distal end of guidewire 28 has moved past the aneurysm neck 38 into the aneurysm 36, catheter 12 is advanced over guidewire 28 such that the extender coil 16 is moved distally along the guidewire by the catheter 12 until the aneurysm treatment device 10 is in place in the aneurysm sac.

In one illustrative embodiment, the length of the expandable liner 24 from its distal end 22 to its proximal end 32 is equal to the straightened length of the extender coil 16 (i.e. its length before retraction of guidewire 28). Thus, there is no slack in the liner as long as guidewire 28 holds coil 16 in the straightened conformation. In another embodiment, coil 16 has sufficient length to slightly stretch liner 24 elastically. This reduces the likelihood that loose material from the unexpanded liner 24 will inhibit travel and positioning of the aneurysm treatment device 10 as it is advanced through the vasculature and positioned in the aneurysm sac. This also reduces the likelihood that liner 24 will occlude the vessel through which it is being advanced.

FIG. 4 illustrates deployment of the aneurysm treatment device 10 within the aneurysm 36. Once device 10 is substantially fully within aneurysm 36, guidewire 28 is retracted proximally, but liner 24 remains connected to delivery catheter 12. The distal end 14 of delivery catheter 12 holds the expandable liner 24 in position within the aneurysm 36 while the expandable liner 24 is filled. Expansion of the liner 24 occurs after the distal end 30 of guidewire 28 is retracted from the extender coil 16.

As shown in FIG. 4, guidewire 28 has been retracted, and extender coil 16 has recoiled away from contact with the delivery catheter 12. Embolic material can now be introduced into liner 24, through catheter 12, using substantially any desired method. Such methods can include, for example, re-introducing guidewire 28 into the interior of liner 24 and advancing coils or particles over guidewire 28 into liner 24, pushing the embolic material through catheter 12 with guidewire 28 completely removed, or infusing or injecting embolic material through catheter 12 into liner 24. The expandable liner 24 is thus filled with a common embolic agent, such as a detachable coil 40. Once liner 24 is filled, it is unable to be removed through the aneurysm neck 38 without retraction of the embolic agent 40. Therefore, once the liner 24 has been filled, it is released from delivery catheter 12, and delivery catheter 12 is removed from the treatment site.

In one illustrative embodiment, extender coil 16 is formed of a small diameter coil, on the order of the detachable coils 40 shown in FIG. 4. However, extender coil 16 can be larger and is illustrated greatly enlarged in the FIGS. for the sake of clarity.

In one illustrative embodiment, the expandable liner 24 has no predetermined shape. Thus, it can fill any given aneurysm shape without exerting unwanted pressure on the wall of the aneurysm.

As mentioned above, in one illustrative embodiment of the present invention, extender coil 16 is given a preformed shape to ensure recoil of extender coil 16 from the proximal end of delivery catheter 12. It is also worth noting that a preformed coil shape, which recoils to a radially expanded conformation, aids in the initial expansion of the agent. Of course, while extender 16 is shown as a coil, it could be any other desired material or shape as well, such as a portion of a tube, etc . . .

Figure 5:
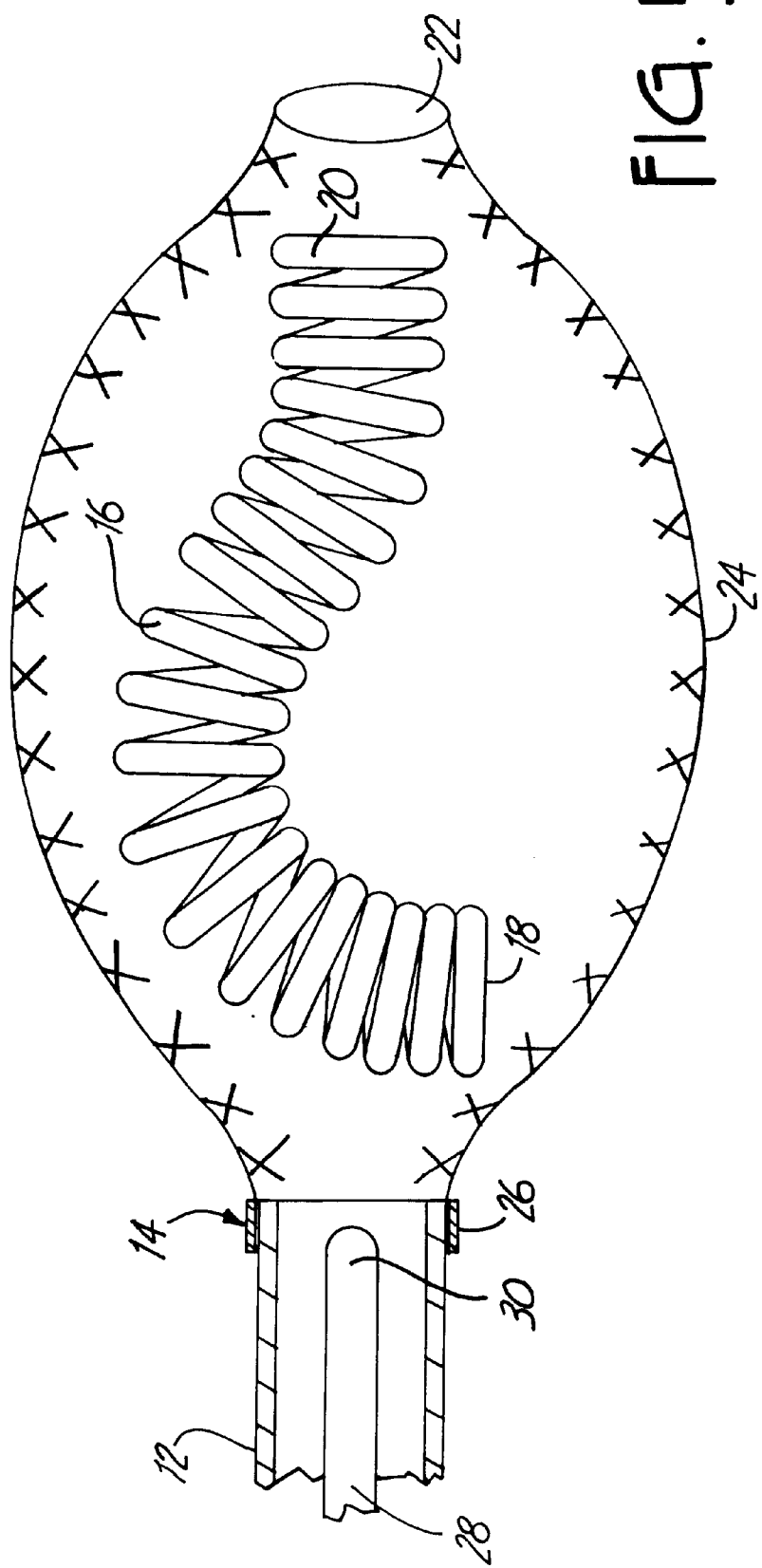
FIGS. 5 and 6 illustrate additional embodiments of the aneurysm treatment device.

In the embodiment, shown in FIG. 5, in which extender 16 floats inside liner 24, when the guidewire 28 is removed from within extender 16, extender 16 moves away from the proximal mouth of liner 24. This allows embolic material to be delivered to liner 24.

Figure 6:
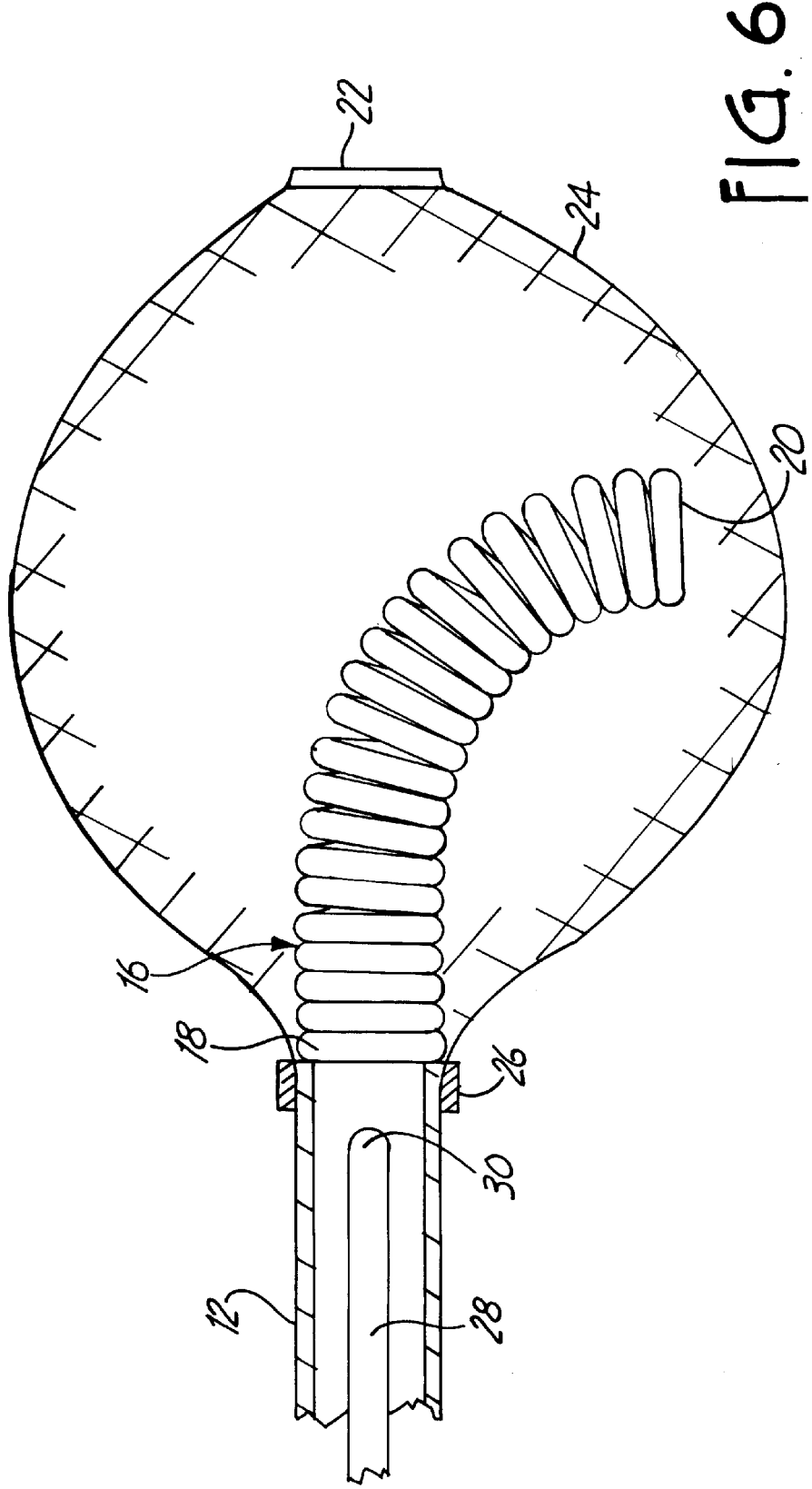

In the embodiment, shown in FIG. 6, in which the proximal end of extender 16 is attached to the proximal end of liner 24, the distal end of extender 16 can either be unattached to, or releasably attached to, the distal end of liner 24. Thus, when guidewire 28 is removed therefrom, the distal end of extender 16 moves away from the distal end of liner 24 such that embolic material can first be delivered to a distal region in liner 24. This helps to ensure a more complete filling of liner 24 and reduces the likelihood of embolic material escaping from the neck of liner 24.

Although the present invention has been described with reference to preferred embodiments, workers skilled in the art will recognize that changes may be made in form and detail without departing from the spirit and scope of the invention.

What is claimed is:

1. A device for treating an aneurysm in a parent vessel, the parent vessel defining a lumen, the aneurysm having a neck and an inner wall defining a cavity communicating with the lumen, the device configured for deployment within the cavity, and comprising:
   an expandable aneurysm liner having an axial length; and
   an extender member having an axial length substantially no greater than the axial length of the expandable liner and being located inside the aneurysm liner wherein the liner and extender member are movable between an insertion position and a deployed position, the liner being in a relatively low profile conformation and the extender member extending longitudinally and having an overall longitudinally elongate conformation when the liner and the extender member are in the insertion position.

2. The device of claim 1 wherein the extender member is radiopaque.

3. The device of claim 1 wherein the extender member floats within the aneurysm liner.

4. The device of claim 1 wherein the aneurysm liner has a proximal end and a distal end and wherein the extender member has a proximal end and a distal end and wherein the proximal end of the extender member is coupled to the proximal end of the aneurysm liner.

5. The device of claim 4 wherein the distal end of the extender member is free of connection with the aneurysm liner.

6. The device of claim 1 wherein the extender member defines a guidewire lumen therethrough.

7. The device of claim 2 wherein the extender member has a distal end connected to a distal end of the aneurysm liner.

8. The device of claim 2 wherein the aneurysm liner has a proximal mouth.

9. The device of claim 8 and further comprising a catheter defining a lumen and having a distal end releasably connected to the proximal mouth of the aneurysm liner such that the inside of the aneurysm liner is in communication with the lumen in the catheter.

10. The device of claim 9 wherein the proximal mouth of the expandable liner is sized to receive an embolic agent.

11. The device of claim 9 wherein the proximal end of the extender member is positionable in the insertion position such that the inside of the aneurysm liner is in communication with the lumen in the catheter.

12. The device of claim 11 wherein the lumen in the catheter comprises a guidewire lumen.

13. The device of claim 12 wherein the extender member is in the insertion position when the guidewire lumen of the catheter is axially aligned with the guidewire lumen of the extender member.

14. The device of claim 13 wherein the liner is elastically stretched when the extender member is in the insertion position.

15. The device of claim 13 wherein the extender member has an axial length which is substantially equal to an axial length of the expandable liner when the expandable liner is in the low profile position.

16. The device of claim 15 and further comprising a guidewire slidably disposed within the guidewire lumen in the extender member and the guidewire lumen in the catheter, wherein the proximal end of the extender member moves away from the delivery catheter upon retraction of the guidewire from within the guidewire lumen in the extender member.

17. The device of claim 16 wherein the extender member is free of connection within the liner upon retraction of the guidewire from within the extender member.

18. The device of claim 16 wherein the extender member comprises a preformed shape that causes the extender member to relax upon retraction of the guidewire.

19. A method of treating an aneurysm in a parent vessel having a lumen, the aneurysm having a neck and an inner wall defining a cavity communicating with the lumen, the method comprising:
   providing a liner having an axial length and an extender member therein and connected thereto, the liner and extender member being movable between a low profile insertion position and an expanded deployed position, the extender member having an axial length substantially no greater than the axial length of the liner, the extender member defining a guidewire receiving passage receiving a guidewire and assuming a longitudinally elongate conformation when in the insertion position;
   endovascularly moving the liner and extender member over the guidewire to a site proximate the aneurysm; and
   deploying the liner within the cavity.

20. The method of claim 19 wherein providing comprises:
   providing a catheter coaxially aligned with, and disconnectably coupled to, a proximal mouth of the liner.

21. The method of claim 20 wherein endovascularly moving comprises:
   maintaining the liner in a relatively low profile insertion position; and
   advancing the extender member and catheter over the guidewire and into the aneurysm.

22. The method of claim 21 wherein deploying the liner comprises:

removing the guidewire from the guidewire receiving passage in the extender member; and expanding the liner.

23. The method of claim 22 wherein the step of expanding the liner includes releasing the extender member into a preformed, radially expanded shape.

24. The method of claim 22 wherein the step of expanding the liner includes filling the liner with an embolic agent.

25. The method of claim 22 wherein deploying further comprises:

detaching the catheter from the aneurysm liner.

26. The method of claim 22 wherein removing the guidewire comprises advancing the liner and extender member distally beyond the guidewire.

27. The method of claim 26 wherein the embolic agent is one of a detachable coil, a liquid polymer, occlusion particles or a combination thereof.

28. A system for treating an aneurysm in a vessel, the aneurysm having an inner wall and a neck defining a cavity, the system comprising:

a catheter having a distal end; and a treatment device disconnectably attached to the catheter;

wherein the treatment device comprises an expandable liner having an axial length, and an extender coil, the liner and extender coil being movable between a low profile insertion position and a radially expanded deployed position, the extender coil having an overall longitudinally elongate conformation when in the insertion position, the extender coil including a distal end attached to the expandable liner and a proximal end coaxially alignable with the distal end of the catheter, the extender coil defining a guidewire lumen, the extender coil having an axial length no greater than the axial length of the liner.

* * * * *

UNITED STATES PATENT AND TRADEMARK OFFICE
CERTIFICATE OF CORRECTION

PATENT NO.    : 6,350,270 B1
DATED         : February 26, 2002
INVENTOR(S)   : Roue It is certified that error appears in the above-identified patent and that said Letters Patent is hereby corrected as shown below:

Column 5,
Lines 64 and 66, replace "2" with -- 6 --.

Signed and Sealed this

Eighteenth Day of February, 2003

JAMES E. ROGAN
*Director of the United States Patent and Trademark Office*